United States Patent [19]

Dern

[11] Patent Number: 5,092,210
[45] Date of Patent: Mar. 3, 1992

[54] HOLDER FOR DISPOSABLE BLADE FOR MICROTOMES AND THE LIKE

[76] Inventor: Klaus Dern, 4645 Dunwoody Club Dr., Dunwoody, Ga. 30350

[21] Appl. No.: 463,345

[22] Filed: Jan. 10, 1990

[51] Int. Cl.$^5$ .............................................. B26D 7/26
[52] U.S. Cl. ......................................... 83/698; 30/49; 83/915.5
[58] Field of Search ................... 83/698, 915.5; 30/49

[56] References Cited

U.S. PATENT DOCUMENTS

| | | | |
|---|---|---|---|
| 3,599,523 | 8/1971 | Pickett | 83/915.5 X |
| 4,207,790 | 6/1980 | Endo | 83/698 |
| 4,700,600 | 10/1987 | Pickett | 83/915.5 X |

FOREIGN PATENT DOCUMENTS 2182881  5/1987  United Kingdom .............. 83/915.5

*Primary Examiner*—Z. R. Bilinsky
*Attorney, Agent, or Firm*—Harry I. Leon

[57] ABSTRACT

A disposable blade holder for use with an apparatus, such as a microtome which is employed in cutting thin sections of tissue and other materials for microscope viewing. The blade holder is removably mountable in a microtome and secured therein by clamps. The holder comprises a cover plate and a base with a pair of small steps slightly greater in height than the thickness of a disposable blade. When a portion of the cover plate, disposed inwardly of the steps and otherwise suspended between them, is subjected to a sufficiently large force directed toward the base, the cover plate is deflected slightly and presses against the blade holding it firmly. The greatest deflection of the cover plate occurs in its mid-section so that the cover plate comes into contact with the blade first before it can touch the remainder of the base. The same clamps used to secure the blade holder itself to the microtome also serve to keep the cover pressed against the blade. This method of securing the blade eliminates the need for the holder to have its own clamping means. The holder, which lacks any moving parts, has only smooth surfaces without any pockets in which to collect debris, facilitating cleaning and sterilization.

10 Claims, 2 Drawing Sheets

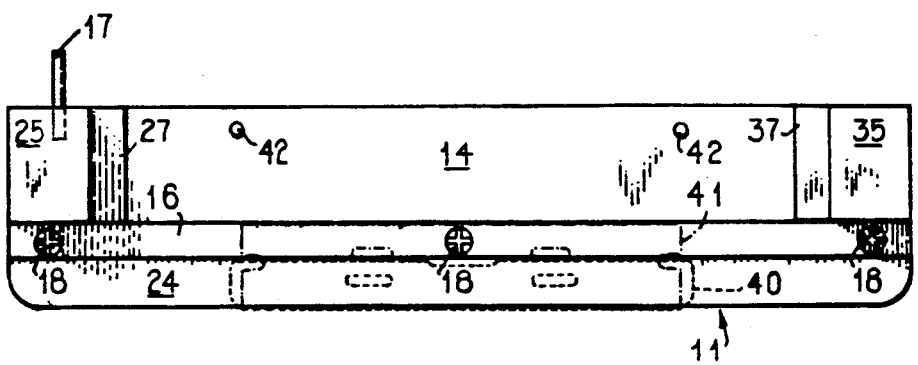
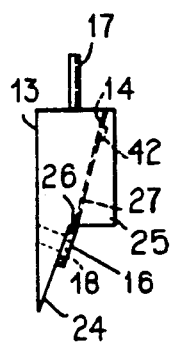
Fig. 2.   Fig. 3.
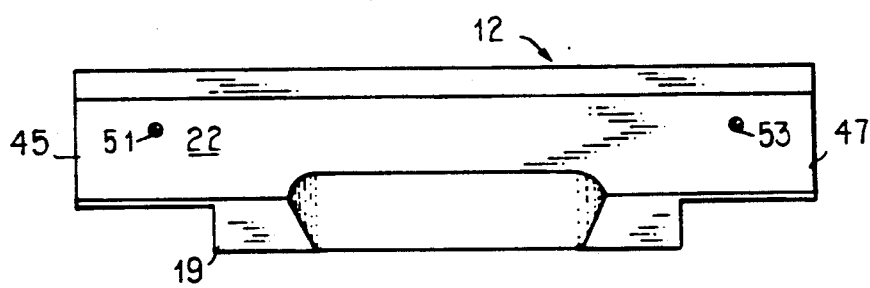
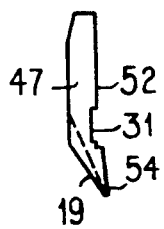
Fig. 4.   Fig. 5.
Fig. 6.
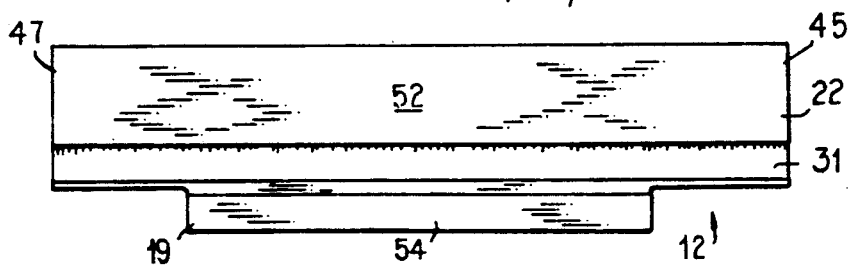

HOLDER FOR DISPOSABLE BLADE FOR MICROTOMES AND THE LIKE

BACKGROUND OF THE INVENTION

This invention relates to holders for disposable blades used in machines such as microtomes in which tissue is cut into thin sections for examination under a microscope.

Elaborate blade holders have been devised for the purpose of securing the blade firmly in place while at the same time allowing one to change blades and to clean the holder. In the Einwegmesserhalter Leitz microtomes, for example, the blade holders comprise several moving parts and many small components, most of which must be disassembled prior to sterilization.

SUMMARY

It is the primary object of this invention therefore to provide a disposable blade holder, mountable in a microtome or the like, in which the blade can be easily installed and which can be readily taken apart and cleaned.

It is a further object of this invention to provide a disposable blade holder in which each structure thereof has only relatively smooth surfaces without pockets to collect debris so that the holder can be easily cleaned and sterilized.

It is a still further object of this invention to provide a disposable blade holder having no moving parts, giving the holder virtually 100% reliability.

In accordance with the present invention, there is provided an improved blade holder for microtomes and the like. The device includes a base and a cover plate. The base, preferably a single, unitary piece formed of metal, comprises a floor with first and second inclined walls separated by a narrow shoulder. At opposite ends of the first inclined wall, each of a pair of steps is situated between the floor and one of a pair of retainer walls. The slope of the steps parallels that of the first inclined wall.

The cover plate includes an elongated segment and a beveled extension having two approximately planar surfaces disposed at a small angle with respect to each other. In the preferred embodiment, this angle is slightly greater than the complement of the angle at which the first and second inclined walls are disposed with respect to each other. When the holder is assembled, the elongated segment fits snugly between the retainer walls; and the planar surface of the elongated segment, which is otherwise spaced apart from the floor, rests upon the steps.

In use, a disposable blade is inserted between the second inclined wall and the beveled extension. With the blade braced against the shoulder or, alternately, against the elongated edge of a spacer disposed parallel to the shoulder, the blade can be positioned so that its sharpened edge protrudes slightly past the front rim of the holder.

Within the assembled holder, the cover plate, acting as a beam simply supported by the steps, is bendable in the direction of the floor. To secure the blade in the holder, clamps are applied to the holder to force a midsection of the elongated segment towards the first inclined wall. Simultaneously, the beveled extension is deflected in a direction toward the floor of the holder. The greatest deflection of the cover plate, as in any situation in which clamping loads are applied to the unsupported portion of a simply supported beam, occurs along a centrally disposed transverse cross-section of the cover plate. When the clamping load has been increased sufficiently, the beveled extension comes into contact with the blade, pressing it against the second inclined wall.

Importantly, the same clamps used to hold the disposable blade in place are employed to retain the holder itself. Most microtomes and the like, including the Leitz, Reichert/Jung and Zeiss "Microm" models, already have a pair of clamps which can be used for these dual functions. But in the prior art, the clamps have been used only to secure a blade holder. Merely by inserting the blade holder of the present invention into a conventional microtome or the like, the clamps can be brought to bear on the holder in such a way as not only to secure the holder in place but also to wedge the blade between the bevelled extension and the second inclined wall, ready for use.

Thus, there is provided a greatly simplified mechanism for holding the blade, thereby eliminating the need for multiple small parts such as have been used in the prior art to clamp the blade independently of the holder.

BRIEF DESCRIPTION OF THE DRAWINGS

FIG. 2 is a plan view of the base of the holder according to FIG. 1;

FIG. 3 is an end view of the base of the holder according to FIG. 1;

FIG. 4 is a plan view of the cover plate of the holder according to FIG. 1;

FIG. 5 is an end view of the cover plate of the holder according to FIG. 1; and

FIG. 6 is a plan view of the underside of the cover plate of the holder according to FIG. 1.

DETAILED DESCRIPTION OF THE PREFERRED EMBODIMENT

Figure 1:
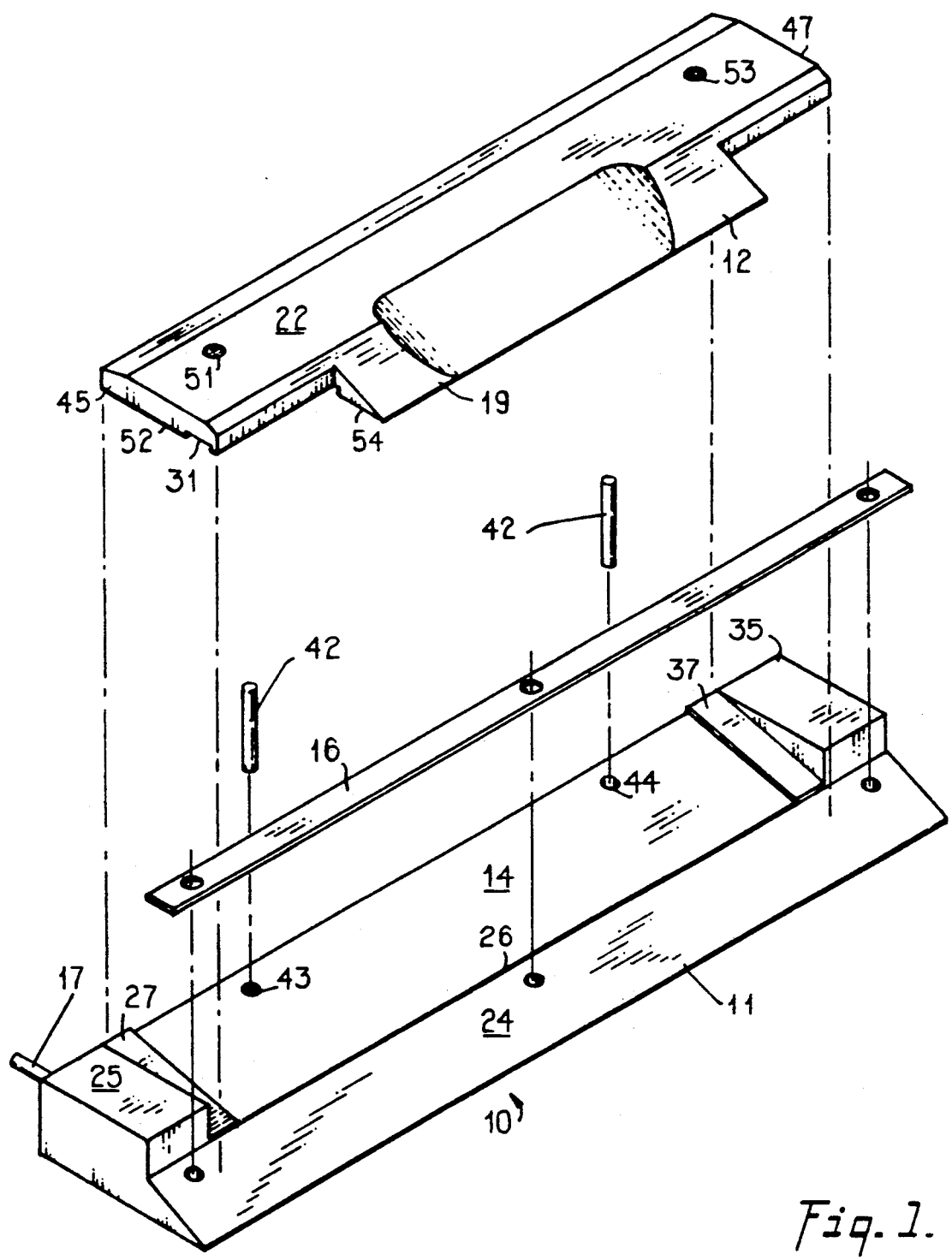
FIG. 1 is an exploded perspective view of the disposable blade holder according to the present invention.

Referring now to the drawings, a disposable blade holder, indicated generally by the numeral 10, comprises a base 11 and a cover plate 12. In the base 11 there are provided first and second inclined walls 14 and 24 and a bottom wall 13. A pair of steps 27, 37 projects upwardly from opposite ends of the first inclined wall 14. The slope of each of the steps 27, 37 parallels that of the first inclined wall 14. The wall 24, which is slightly depressed in elevation relative to the wall 14, forms a shoulder 26 with it. In addition, retainer walls 25, 35 bound the distal ends of the steps 27, 37, respectively, and extend upwardly at approximately right angles thereto.

The cover plate 12 includes an elongated segment 22 and a beveled extension 19 having two approximately planar surfaces 52 and 54, respectively, situated on either side of an elongated, shallow groove 31 formed in the segment. The planes in which the surfaces 52, 54 lie are disposed at an angle of about 6 degrees with respect to each other. Measuring, by way of example, approximately 8.0 cm in length and 6 mm in width, the edge of the surface 54 closest the groove 31 is disposed about 0.13 mm below the plane of the surface 52. In the assembled holder 10, the surfaces 52 and 54 are contiguous with the steps 27, 37 and with the second inclined wall 24, respectively, of the base 11.

The base 11 measures, by way of example, 15 cm in length and 3.5 cm in width. Exemplary dimensions of the cover plate 12 are 12.9 cm in length and, at the mid-section and at the distal ends of the plate, 3.2 cm and 2.4 cm, respectively, in width. Both the base 11 and the cover plate 12 are preferably fabricated from a metal such as No. 304 stainless steel; but other metals and plastics are also suitable.

In the preferred embodiment, the inclined wall 24 on which the disposable blade 40 rests is at an angle of approximately 20 degrees with respect to the bottom wall 13. The inclined wall 14, on the other hand, is inclined at angle of approximately 15 degrees with respect to the bottom wall 13. When the cover plate 12 is mounted above the base 11, the wall 24 and the surface 54 on the beveled extension 19 are approximately parallel and approximately 0.56 mm apart.

In use, a narrow disposable blade 40 is placed within the holder 10 between the base 11 and the cover plate 12. The back edge of the blade 40 abuts a thin spacer 16 mounted against the shoulder 26 and held in place by screws 18. The groove 31 in the cover plate 12 is slightly wider than the spacer 16 so that the cover plate, when mounted for use on the base 11, straddles the spacer. Alternately, the spacer 16 can be removed by withdrawing the screws 18 to accommodate a wide disposable blade 41. In the latter case, the blade 23 rests against the shoulder 26.

To facilitate positioning the cover plate 12 on the base 11, first alignment pins 42 force-fitted into holes 43, 44 in the base provide stops for the cover plate. Further, the elongated segment 22 fits, with close tolerance, between the retainer walls 25, 35 of the base 11. In the preferred embodiment, the distance between the retainer walls 25 and 35 is only approximately 0.1 mm greater than the length of the elongated segment 22. With the cover plate 12 abutting the pins 42 and positioned between the retainer walls 25, 35, the cover plate is properly aligned with the base 11 for mounting in a microtome (not shown) or the like.

So aligned, the cover plate 12 rests in part upon the steps 27, 37. The steps 27, 37 are greater in height than the first inclined wall 14 by at least the thickness of either the narrow blade 13 or the wide blade 23. The height of each of the steps 27, 37 above the first inclined wall 14 measures, by way of example, about 0.7 mm whereas a small blade 40 is typically only about 0.25 mm thick and a large blade 41 about 0.30 mm thick.

Securing an assembly comprising the holder 10 and the blade 40 or 41 in a machine (not shown) such as the Leitz 1512/1516 rotary microtome or the Leitz 1720 digital cryostats involves holding the assembly with blade holder clamps (not shown). To facilitate positioning the assembly under these clamps, there is provided a second alignment pin 17 which protrudes rearwardly from the base 11. The clamps are conventional parts of microtomes, cryostats, and like machines. The blade holder clamps contact the cover plate 12 at indents 51, 53. As the clamps are tightened, the cover plate 12 bends slightly, deflecting the mid-section of the bevelled extension 19 in a direction toward the second inclined wall 24.

When sufficient clamping force is applied to the cover plate 12 at the indents 51, 53, the bevelled extension 19 presses the blade 40, 41 against the second inclined wall 24. The surface 54 on the beveled extension 19 is disposed at such an angle (5 to 6 degrees) with respect to the surface 52 that the surface 54 is the first one on the cover plate 12 to come into contact with the blade 40, 41 when said clamping force is applied. Further, since the angle between the surfaces 52 and 54 is slightly larger than 5 degrees, the surface 54 comes into contact first near the cutting edge of blade 40, 41. In a situation in which a small disposable blade 40 is to be secured in the holder 10, the deflection of the beveled extension 19 covers a distance of approximately 0.3 mm. When a large blade 41 is positioned for use, on the other hand, the mid-section of the beveled extension 19 is deflected through a distance of approximately 0.25 mm.

Thus, with the holder 10, the same clamp which is used to hold the holder in the microtome secures the blade 40, 41 firmly in place. Moreover, once the holder 10 with either the small blade 40 or the large blade 41 abutting the spacer 16 or the shoulder 26, respectively, is positioned in the microtome, the clamping force is easily applied. Indeed, a user need exert no more effort than is ordinarily required to secure a holder by itself in the microtome. Further, the holder 10, lacking as it does any built-in complex clamping device, can be readily disassembled and cleaned.

It is apparent from the foregoing that a new and improved disposal blade holder for microtomes and the like has been provided. While only the presently preferred embodiment of the invention has been disclosed, as will be apparent to those familiar with the art, certain changes and modifications can be made without departing from the scope of the invention as defined by the following claims.

What is claimed is:

1. A holder adapted to secure a disposable blade in a tissue-cutting machine in which the machine includes means for clamping the holder in position, wherein the improvement comprises:

(a) a base having a pair of steps and an inclined wall disposed between the steps, the slope of each of the steps being approximately parallel to that of the inclined wall, the height of each of the steps being slightly greater than the thickness of the blade; and (b) a cover plate, the ends of the cover plate being supported by the steps so that the cover plate can act as a beam, the cover plate being deflected towards the inclined wall when sufficient force is applied with the clamping means to points on the cover plate disposed inwardly of the steps, the blade being wedged between the cover plate and the base when the mid-section has been sufficiently deflected towards the inclined wall.

2. The holder according to claim 1, wherein the improvement further comprises a shoulder which defines an edge of said inclined wall, the shoulder forming a stop against which the blade abuts.

3. The holder according to claim 1, wherein the improvement further comprises a shoulder which defines an edge of said inclined wall and an elongated spacer disposed contiguous with and parallel to said edge, the spacer forming a stop against which the blade abuts.

4. A holder adapted to secure a disposable blade in a microtome in which the microtome includes means for clamping the holder in position, wherein the improvement comprises:

a base and a cover plate between which the blade can be inserted, the base having a pair of steps and an inclined wall disposed between the steps, the slope of each of the steps being approximately parallel to that of the inclined wall, the height of each of the steps being slightly greater than the thickness of the blade; the ends of the cover plate being supported by the steps so that the cover plate can act as a beam, the cover plate being deflected towards the inclined wall when sufficient force is applied with the clamping means to points on the cover plate disposed inwardly of the steps, the blade being wedged between the cover plate and the base when the mid-section has been sufficiently deflected towards the inclined wall.

5. The holder according to claim 4, wherein the improvement further comprises means including a pair of retainer walls which protrude upwardly from the base along the distal edges of the steps for holding the cover plate in position relative to the base.

6. In a holder adapted to secure a disposable blade in a microtome which includes means for clamping the holder itself in position in the microtone, wherein the improvement comprises:

a base and a cover plate between which the blade is held, the cover plate being deflectable in the direction of the base upon the application of force using the same clamping means employed to clamp the holder itself in position in the microtome, so that the blade, as it is being held between the base and the cover plate, can be wedged between them in a fixed position using only the force of said clamping means.

7. The holder according to claim 1 wherein the base further comprises first and second inclined walls, the first inclined wall being the inclined wall disposed between the steps, and wherein the cover plate is further characterized as having first and second approximately planar faces disposed contiguous with the first and second inclined walls, respectively; the second planar face being spaced apart from the second inclined wall, the space between the second planar face and the second inclined wall decreasing in a direction away from the steps, so that the second planar face first contacts the blade near its cutting edge as the cover plate is deflected toward the first inclined wall.

8. The holder according to claim 1 which further comprises means for bringing the cover plate into contact with the blade near an edge thereof disposed away from the steps before the cover plate is brought into contact with the remainder of the blade when the cover plate is deflected toward the inclined wall.

9. A holder adapted to secure a disposable blade in a tissue-cutting machine in which the machine includes means for clamping the holder itself in position in the machine, wherein the improvement comprises:

a base and a cover plate between which the blade can be inserted, the base having an inclined wall on which the blade can be placed; a portion of the transverse cross-section of the cover plate being deflected towards the inclined wall when sufficient force, directed toward the base, is applied with said clamping means to points on the cover plate disposed distal from the inclined wall, the entire transverse cross-section being separated, by at least the thickness of the disposable blade, from the base when said force directed toward the base is released, the blade being wedged between the cover plate and the base when said portion of the transverse cross-section has been sufficiently deflected towards the base.

10. A holder adapted to secure a disposable blade in a microtome in which the microtome includes means for clamping the holder itself in position in the microtome, wherein the improvement comprises:

a base and a cover plate between which the blade can be inserted, the base having means for separating the transverse cross-section of the cover plate from the base by at least the thickness of the disposable blade blade, the ends of the cover plate being supported by the separating means so that the cover plate can act as a beam, the cover plate being deflected towards the base when sufficient force is applied, in a direction towards the base, with said clamping means to points on the cover plate disposed inwardly of the separating means, the blade being wedged between the cover plate and the base when the mid-section of the cover plate has been sufficiently deflected towards the base.

* * * * *